(12) United States Patent
Miyaji et al.

(10) Patent No.: US 10,485,508 B2
(45) Date of Patent: Nov. 26, 2019

(54) ULTRASONIC DIAGNOSTIC DEVICE

(71) Applicant: Hitachi, Ltd., Tokyo (JP)

(72) Inventors: Kagami Miyaji, Kanagawa (JP);
Keiichi Itatani, Kanagawa (JP);
Tomohide Nishiyama, Tokyo (JP);
Hajime Sakashita, Tokyo (JP);
Yoshinori Seki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 297 days.

(21) Appl. No.: 15/320,164

(22) PCT Filed: May 29, 2015

(86) PCT No.: PCT/JP2015/065613
§ 371 (c)(1),
(2) Date: Dec. 19, 2016

(87) PCT Pub. No.: WO2015/198794
PCT Pub. Date: Dec. 30, 2015

(65) Prior Publication Data
US 2017/0128035 A1    May 11, 2017

(30) Foreign Application Priority Data
Jun. 27, 2014   (JP) ................................. 2014-131999

(51) Int. Cl.
*A61B 8/06* (2006.01)
*A61B 8/00* (2006.01)
*A61B 8/08* (2006.01)
(52) U.S. Cl.
CPC ................ *A61B 8/06* (2013.01); *A61B 8/463* (2013.01); *A61B 8/488* (2013.01); *A61B 8/5207* (2013.01); *A61B 8/5215* (2013.01)

(58) Field of Classification Search
CPC .......... A61B 8/06; A61B 8/463; A61B 8/488; A61B 8/5207; A61B 8/5215
See application file for complete search history.

(56) References Cited

U.S. PATENT DOCUMENTS

| 4,768,515 A | 9/1988 | Namekawa |
| 5,947,903 A | 9/1999 | Ohtsuki et al. |

(Continued)

FOREIGN PATENT DOCUMENTS

| CN | 101919711 A | 12/2010 |
| CN | 101919712 A | 12/2010 |

(Continued)

OTHER PUBLICATIONS

International Preliminary Report on Patentability received for PCT Patent Application No. PCT/JP2015/065613, dated Jan. 5, 2017, 11 pages.

(Continued)

*Primary Examiner* — Paula J Stice

(57) ABSTRACT

An ultrasonic diagnostic device wherein: a Doppler processing unit acquires Doppler information in a living body on the basis of an ultrasonic reception signal; a velocity vector calculating unit acquires the velocity vector distribution of a blood stream in the living body on the basis of the Doppler information in the living body; and, to form a flow line showing the flow of the blood stream on the basis of the velocity vector distribution, a flow line forming unit searches for a proper start point by inversely tracing the flow of the blood stream from an initial start point along the reverse direction of the velocity vector and then forms a flow line extended from the proper start point.

15 Claims, 8 Drawing Sheets

(56) References Cited

U.S. PATENT DOCUMENTS

| | | |
|---|---|---|
| 2008/0269611 A1 | 10/2008 | Pedrizzetti et al. |
| 2009/0326379 A1* | 12/2009 | Daigle ............... A61B 8/06 |
| | | 600/453 |
| 2013/0172744 A1 | 7/2013 | Kim |
| 2013/0172747 A1 | 7/2013 | Kim et al. |
| 2013/0172755 A1 | 7/2013 | Kim et al. |
| 2015/0013471 A1 | 1/2015 | Ono et al. |

FOREIGN PATENT DOCUMENTS

| | | |
|---|---|---|
| CN | 103181790 A | 7/2013 |
| JP | S62152439 A | 7/1987 |
| JP | 200744408 | 2/2007 |
| JP | 2007044408 A | 2/2007 |
| JP | 2008583 | 1/2008 |

OTHER PUBLICATIONS

Itatani et al., "The novel Insights into Cardiovascular Imaging Techniques with the Flow Visualization Method:The present conditions and the prospects of the Echocardiography Flow Visualization Method named VFM (Vector Flow Mapping)", MEDIX, 2014, vol. 60, 5 pages.
Office Action received for Japanese Patent Application No. JP2014-131999, dated Aug. 8, 2015, 4 pages English translation.
International Search Report received for Japanese Patent Application No. JP2014-131999, dated Aug. 25, 2015, 5 pages including 2 pages English translation.
Chinese Office Action issued for Chinese application No. 201560033786. X, dated Dec. 27, 2018, 16 pages.

\* cited by examiner

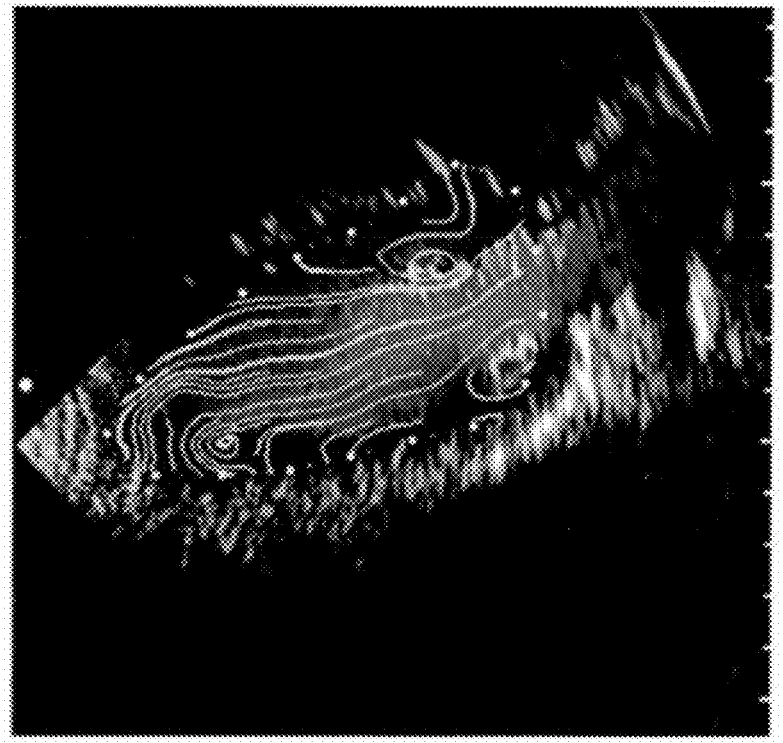
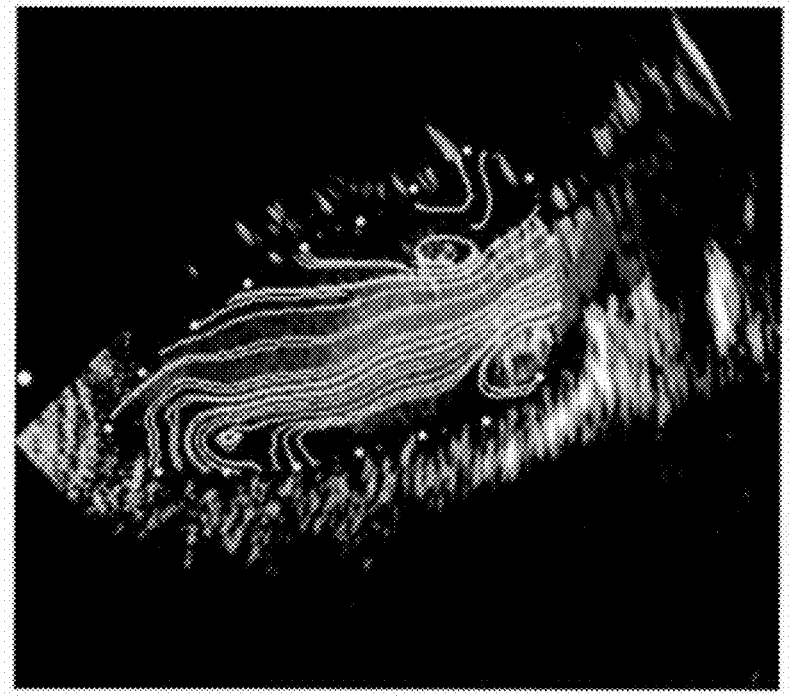
FIG. 6

ULTRASONIC DIAGNOSTIC DEVICE

CROSS-REFERENCE TO RELATED APPLICATIONS

This application is a national phase claiming the benefit of and priority to International Patent Application No. PCT/JP2015/065613, entitled "ULTRASONIC DIAGNOSTIC DEVICE", filed May 29, 2015, which claims priority to Japanese Patent Application No. 2014-131999, entitled "ULTRASONIC DIAGNOSTIC DEVICE", filed Jun. 27, 2014, which are hereby incorporated by reference in their entireties.

TECHNICAL FIELD

The present invention relates to an ultrasonic diagnostic device, and particularly to a technique for forming a streamline indicating a flow of fluid.

BACKGROUND

Techniques known in the art include obtaining, based on a received signal generated by transmitting and receiving ultrasonic waves with respect to fluid such as blood flow, diagnosis information regarding the fluid. Patent Document 1, for example, describes a technique of obtaining, based on a received signal (echo data) obtained by transmitting and receiving ultrasonic waves with respect to fluid within a human body, two-dimensional velocity vectors regarding the fluid at a plurality of points within an observation plane. It is possible to extract, from a distribution of the two-dimensional velocity vectors at a plurality of points within the observation plane, diagnosis information such as a streamline representing a flow of fluid. Application of such information to diagnosis of a heart, for example, is expected.

CITATION LIST

Patent Literature

Patent Document 1: JP-A-2013-192643

SUMMARY

Technical Problem

In consideration of the background art described above, the inventors of the present application have repeated research and development concerning techniques of obtaining diagnosis information of a heart by utilizing ultrasonic waves, and particularly focused attention on a technique for forming a streamline indicating a flow of fluid.

The present invention was achieved in the process of the research and development, and is directed to providing an improved technique for forming a streamline indicating a flow of fluid by utilizing ultrasonic waves.

Solution to Problem

In accordance with the above object, an ultrasonic diagnostic device includes a probe configured to transmit and receive an ultrasonic wave, a transmitter and receiver unit configured to control the probe to obtain a received signal of an ultrasonic wave from an interior of a human body, a Doppler processing unit configured to obtain Doppler information of the interior of the human body based on the received signal of an ultrasonic wave, a vector computation unit configured to obtain a distribution of motion vectors of fluid in the human body based on the Doppler information of the interior of the human body, and a streamline forming unit configured to form a streamline indicating a flow of fluid based on the distribution of the motion vectors by inversely tracking the flow of fluid from an initial start point in a direction opposite the motion vectors to search for a proper start point and forming a streamline extending from the proper start point.

In the above device, the motion vector refers to vector information related to a motion of fluid, and specifically includes, for example, a velocity vector indicating the velocity and direction at each portion within the fluid and a shift vector indicating an amount and direction of shift at each portion. Although the distribution of the motion vectors can be obtained using the technique described in Patent Document 1 (a distribution of the two-dimensional velocity vectors), other known techniques may also be used to obtain the distribution of the motion vectors.

The above device inversely tracks a flow of fluid in a direction opposite the motion vectors from the initial start point to search for a proper start point, and forms a streamline extending from the proper start point. More specifically, the proper start point is searched for from the initial start point, in the direction opposite to the motion vectors, that is, upstream of the flow, so that a streamline having its origin at the proper start point is formed. When a streamline is formed and shown only downstream from the initial start point and is not shown upstream from the initial start point, contrary to the above device, such a streamline is shown to be interrupted at the initial start point. The above device, on the other hand, searches for the proper start point toward upstream from the initial start point to form a streamline extending from the proper start point, so that a natural streamline which is continuous from the initial start point can be formed.

In some preferable specific examples, the streamline forming unit may be configured to inversely track the flow of fluid by sequentially tracing back a tracking point located in the direction opposite the motion vectors from the initial start point.

In some preferable specific examples, the streamline forming unit may be configured to designate a tracking point which satisfies a condition for terminating inverse tracking as the proper start point.

In some preferable specific examples, the streamline forming unit may be configured to track the flow of fluid in a direction of the motion vectors from the proper start point to thereby form the streamline extending from the proper start point.

In some preferable specific examples, the streamline forming unit may be configured to inversely track the flow of fluid in the direction opposite the motion vectors from the initial start point to form an upstream streamline from the initial start point to the proper start point, to track the flow of fluid in the direction of the motion vectors from the initial start point to form a downstream streamline from the initial start point, and to connect the upstream streamline and the downstream streamline to form a streamline extending from the proper start point toward downstream through the initial start point.

In some preferable specific examples, display processing may be applied, to the streamline formed by the streamline forming unit, in accordance with the direction of the flow on the streamline to form a display image of the streamline.

In some preferable specific examples, display processing may be applied, to the streamline formed by the streamline forming unit, in accordance with the flow rate on the streamline to form a display image of the streamline.

In accordance with a further aspect, a fluid information processing device includes a vector computation unit configured to obtain, based on Doppler information within a human body obtained using ultrasonic waves, a distribution of motion vectors of fluid within the human body, and a streamline forming unit configured to form a streamline indicating a flow of fluid based on the distribution of motion vectors by inversely tracking the flow of fluid from an initial start point in a direction opposite the motion vectors to search for a proper start point and forming a streamline extending from the proper start point.

The fluid information processing device described above can be implemented, for example, by a computer. Specifically, it is possible to cause a computer to function as the fluid information processing device described above using a program. The program causes the computer to implement a vector computation function to obtain a distribution of the motion vectors of fluid within a human body based on Doppler information within the human body obtained by using ultrasonic waves. The program also causes the computer to implement a streamline forming function to form a streamline indicating a flow of fluid based on the distribution of the motion vectors by inversely tracking a flow of fluid in a direction opposite to the motion vector from the initial start point to search for a proper start point and forming a streamline extending from the proper start point. The program may be stored in a computer-readable storage medium such as a disk and memory and provided to the computer via the storage medium or via an electric communication line such as the Internet.

Advantageous Effects of Invention

The present invention is directed to providing an improved technique for forming a streamline indicating a flow of fluid using ultrasonic waves. According to some preferable aspects, a proper start point is searched for upstream from an initial start point and a streamline extending from the proper start point is formed, so that a natural continuous streamline can be formed upstream from the initial start point.

BRIEF DESCRIPTION OF DRAWINGS

FIG. 6 illustrates specific example display images of streamlines.

DESCRIPTION OF EMBODIMENTS

Figure 1:
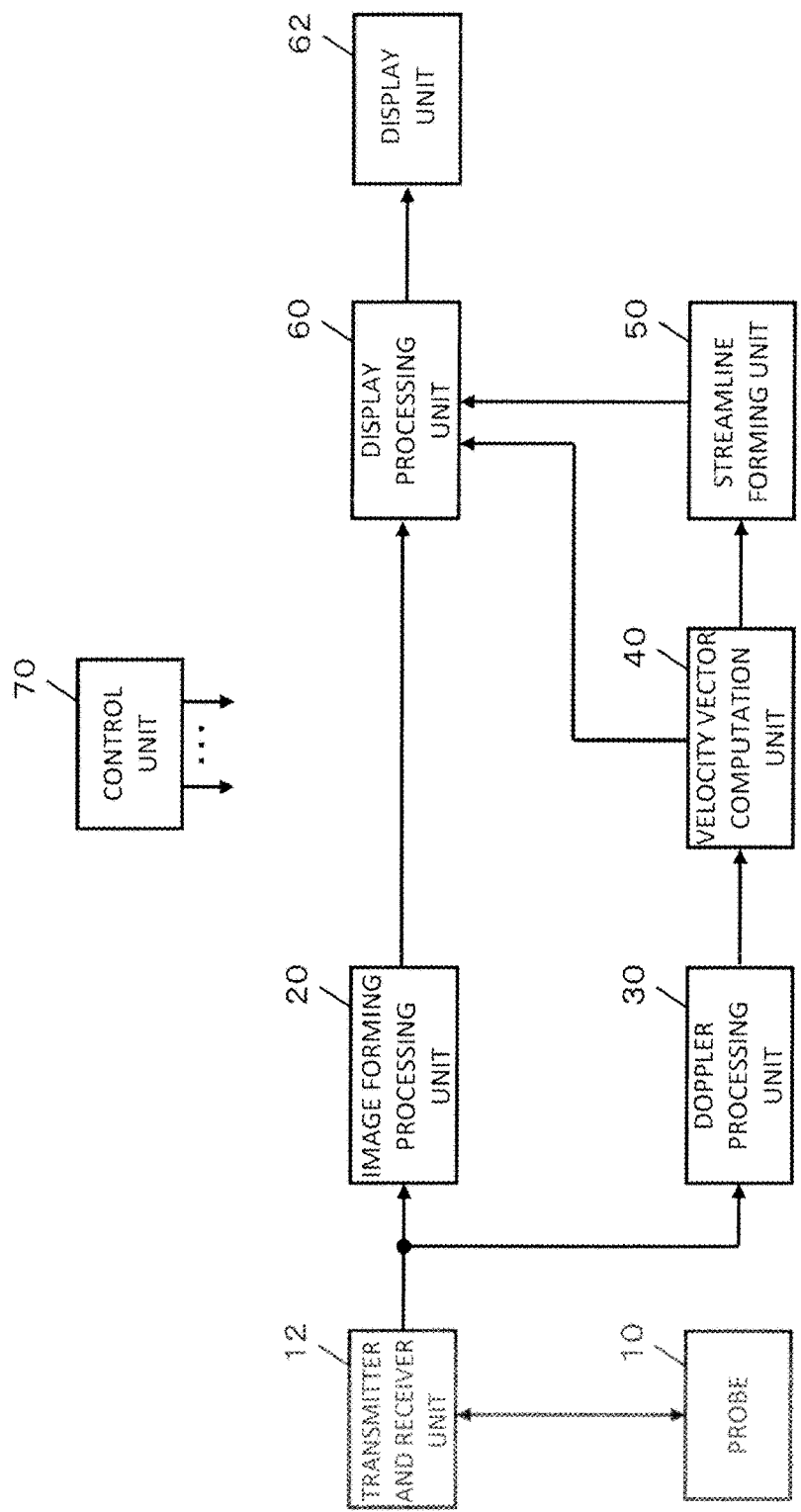
FIG. 1 is a diagram illustrating a whole structure of an ultrasonic diagnostic device according to an embodiment of the present invention.

FIG. 1 is a diagram illustrating a whole structure of an ultrasonic diagnostic device according to a preferable embodiment of the present invention. The ultrasonic diagnostic device illustrated in FIG. 1 has a function to form a streamline indicating a flow of fluid within a human body and therefore can form a streamline of a blood flow flowing in a blood vessel or within other internal organs, for example. A subject of diagnosis may preferably be a blood flow within the heart. The following description therefore specifies a blood flow within the heart, which is a preferable example fluid within a human body, as a subject of diagnosis.

A probe 10 is an ultrasound probe which transmits and receives ultrasonic waves to and from a region within a human body including the heart. The probe 10 includes a plurality of transducer elements, which are electronically scan-controlled to scan an ultrasound beam within a space including the heart. The probe 10 is held by a user (examiner) such as a doctor and is used in contact with a body surface of a subject. The probe 10 may be inserted into a body cavity of the subject for use or may be a probe which performs both electronic scanning and mechanical scanning.

A transmitter and receiver unit 12 has a function as a transmitting beam former and a received beam former. Specifically, the transmitter and receiver unit 12 outputs a transmitting signal to each of the plurality of transducer elements of the probe 10 to thereby form a transmitting beam, and further applies phase alignment and summation processing, for example, to a plurality of received signals obtained from the plurality of transducer elements to thereby form a received beam. Thus, an ultrasound beam (the transmitting beam and the received beam) is scanned within a scanning plane and a received signal is formed along the ultrasound beam. To obtain the received signal of ultrasonic waves, an ultrasound beam may be scanned within a three-dimensional space in a stereoscopic manner, or a technique, such as transmission aperture synthesis, may be used.

An image forming processing unit 20, based on the received signal of ultrasonic waves obtained from the scanning plane, forms data for an ultrasound image (image data). The image forming processing unit 20 applies detection processing, filter processing, AD conversion processing, and other processing to the received signal of ultrasonic waves to form frame data for a B-mode image. Image data concerning a known ultrasound image other than a B-mode image may also be formed.

The image forming processing unit 20 forms image data in a scanning coordinate system corresponding to scanning of ultrasonic waves, such as an rθ coordinate system based on the r-direction corresponding to the depth direction of the beam and the θ-direction corresponding to the scanning direction of the beam. The image data obtained in the scanning coordinate system (e.g., the rθ coordinate system) undergoes coordinate transformation processing, for example, by a digital scan converter or other device, and is converted to image data of a display coordinate system (e.g., xy orthogonal coordinate system). The function of the digital scan converter is provided by the image forming processing unit 20 or a display processing unit 60.

A Doppler processing unit 30 measures a Doppler shift amount contained in the received signal obtained along the ultrasound beam. The Doppler processing unit 30 specifically measures a Doppler shift amount (Doppler shift frequency) occurring within the received signal of ultrasonic waves due to a blood flow, by using known Doppler processing, for example, to obtain velocity information concerning the blood flow in the ultrasound beam direction.

A velocity vector computation unit 40, based on the velocity information concerning the blood flow in the ultrasound beam direction, forms a distribution of two-dimensional velocity vectors within the scanning plane. The velocity vector computation unit 40 uses the velocity information concerning the blood flow in the ultrasound beam direction and motion information of the cardiac wall to obtain two-dimensional velocity vectors of the blood flow at each location within the scanning plane, as described in Patent Document 1 (JP 2013-192643 A), for example.

The two-dimensional velocity vector distribution within the scanning plane can be formed from one-dimensional velocity information along the ultrasound beam direction using various known methods. The two-dimensional velocity vectors may also be formed by forming two ultrasound beams in different directions and obtaining velocity information from each of the two ultrasound beams.

The velocity vector computation unit 40 obtains the velocity vector at each of a plurality of sample points in the scanning coordinate system (e.g., the rθ coordinate system) corresponding to scanning of the ultrasonic waves, to form the two-dimensional velocity vector distribution. The velocity vector computation unit 40 further obtains, from the two-dimensional distribution of the velocity vectors obtained in the scanning coordinate system (e.g., the rθ coordinate system), a distribution of two-dimensional velocity vectors in the display coordinate system (e.g., the xy orthogonal coordinate system), by coordinate transformation processing or the interpolation processing. The coordinate transformation processing or the interpolation processing concerning the two-dimensional velocity vector distribution may be performed in a streamline forming unit 50.

The streamline forming unit 50, based on the distribution of the two-dimensional velocity vectors obtained in the velocity vector computation unit 40, forms a streamline indicating a flow of a blood flow within the heart, which is a specific example fluid. Specific processing performed in the streamline forming unit 50 will be described below.

The display processing unit 60 forms a display image, based on the image data of an ultrasound image formed by the image forming processing unit 20, the distribution of the velocity vectors obtained by the velocity vector computation unit 40, and the streamlines formed by the streamline forming unit 50. The display image formed in the display processing unit 60 is displayed on a display unit 62.

A control unit 70 controls the whole ultrasonic diagnostic device illustrated in FIG. 1. The ultrasonic diagnostic device in FIG. 1 may preferably include an operation device, such as a mouse, a keyboard, a trackball, a touch panel, and a joy stick. An instruction received by a user via the operation device, for example, is also reflected in the whole control performed by the control unit 70.

Among the elements (the units designated by reference numerals) illustrated in FIG. 1, the transmitter and receiver unit 12, the image forming processing unit 20, the Doppler processing unit 30, the velocity vector computation unit 40, the streamline forming unit 50, and the display processing unit 60 may be implemented by using hardware such as an electrical or electronic circuit or a processor, for example, and a device such as a memory may be used for the implementation. The function corresponding to each unit described above may be implemented by cooperation of hardware such as a CPU, a processor, and a memory, and software (program) which regulates the operation of the CPU or the processor. A specific example of the display unit 62 may include a liquid crystal display, for example. The control unit 70 can be implemented by cooperation of hardware such as a CPU, a processor, and a memory, and software (program) which regulates the operation of the CPU or the processor.

The ultrasonic diagnostic device illustrated in FIG. 1 has been summarized as above. Specific example functions to be implemented by the ultrasonic diagnostic device of FIG. 1 will now be described in detail. The following description concerning the elements (the sections denoted by reference numerals) illustrated in FIG. 1 uses the reference numerals in FIG. 1.

Figure 2:
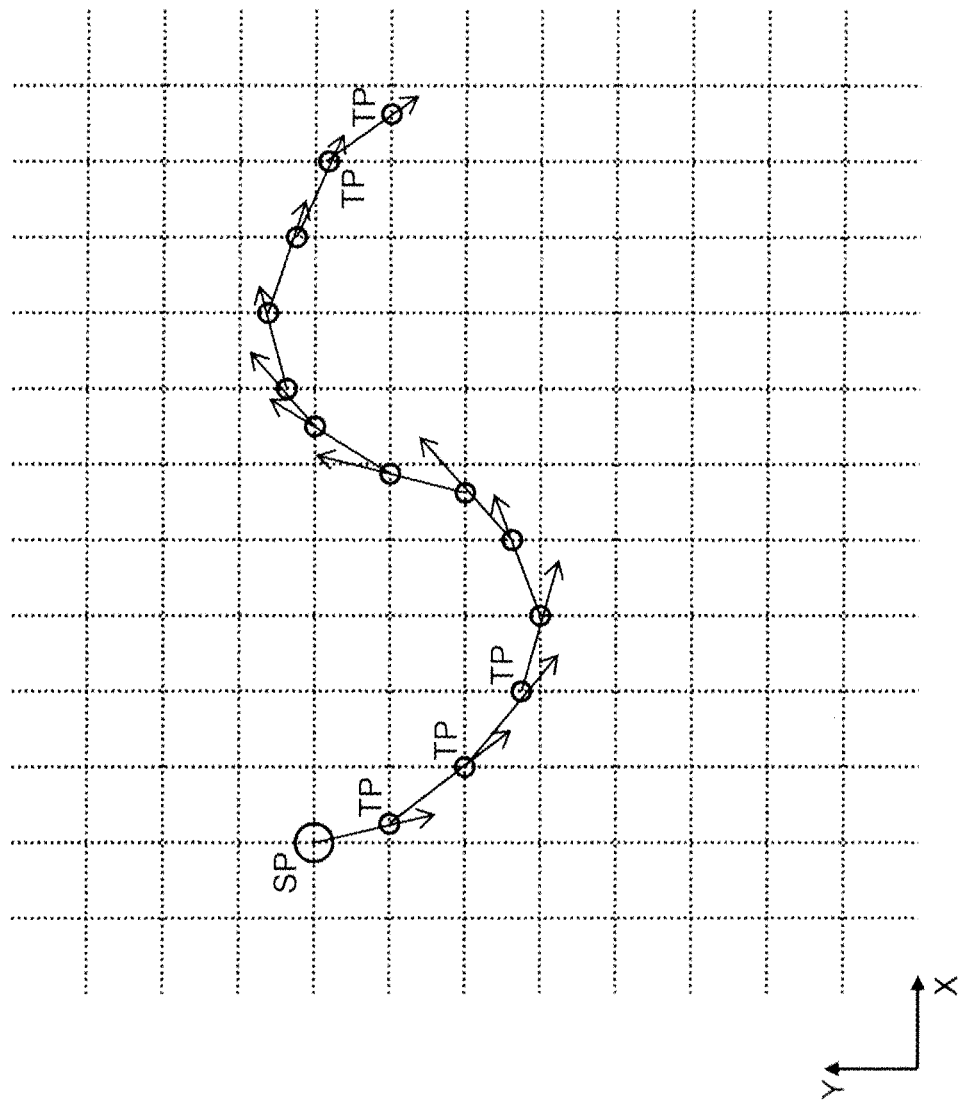
FIG. 2 is a diagram for explaining specific example processing for tracking a flow of fluid.

FIG. 2 is a diagram for explaining specific example processing for tracking the flow of fluid. The streamline forming unit 50 tracks the flow of a blood flow within a plane in which a distribution of two-dimensional velocity vectors related to the blood flow is obtained. The streamline forming unit 50, for each of a plurality of start points SP, tracks the flow of fluid starting from each start point SP (preferably a proper start point which will be described below) as an origin in accordance with the distribution of the two-dimensional velocity vectors. FIG. 2 shows only a single start point SP as a representative example.

The streamline forming unit 50 starts tracking, from a start point SP, in the direction of the velocity vector at the location of the start point SP (an arrow in FIG. 2) to search for a tracking point TP. The tracking point TP is searched for on an operation grid in a lattice shape, for example, shown by dashed lines. After locating the tracking point TP on the operation grid, tracking is continued in the direction of the velocity vector at the tracking point TP, to search for the next tracking point TP.

When the velocity vector does not exist at the location of the tracking point TP, an interpolated vector is obtained by interpolation processing or other processing, based on a plurality of velocity vectors which have already been computed near the tracking point TP, and is used as a velocity vector at the tracking point TP.

As illustrated in FIG. 2, the tracking points TP are thus sequentially searched for in accordance with the distribution of velocity vectors, starting from the single start point SP, for tracking the flow of a blood flow. The streamline forming unit 50 executes the tracking within a region of interest which is set with respect to a cardiac cavity in the heart, for example, until a result of the tracking reaches a border of the region of interest. The streamline forming unit 50 may terminate the tracking when the velocity vector reaches the lower limit reference value or less or when the length (distance) of the tracking reaches the upper limit value, in the course of the tracking.

Upon termination of the tracking, the streamline forming unit 50 connects, among each start point SP and a plurality of tracking points TP obtained from the start point SP, adjacent points by a straight line or a curved line, thereby forming a polygonal or curved streamline.

When a streamline is formed by tracking only in the direction of the velocity vectors (forward trace) starting from each start point SP, the streamline is formed downstream of the start point SP (an "initial start point" which will be described below) but is not formed upstream of the start point SP. This makes the displayed streamline appear to be interrupted at the start point SP. A streamline within the cardiac cavity having no upstream portions, for example, may be discontinuous and unnatural.

The streamline forming unit 50 therefore searches for a start point which is proper (proper start point) upstream from an original start point SP (initial start point), and forms a streamline starting from the proper start point. In searching for the proper start point, the streamline forming unit 50 tracks the flow of a blood flow inversely (back trace).

Figure 3:
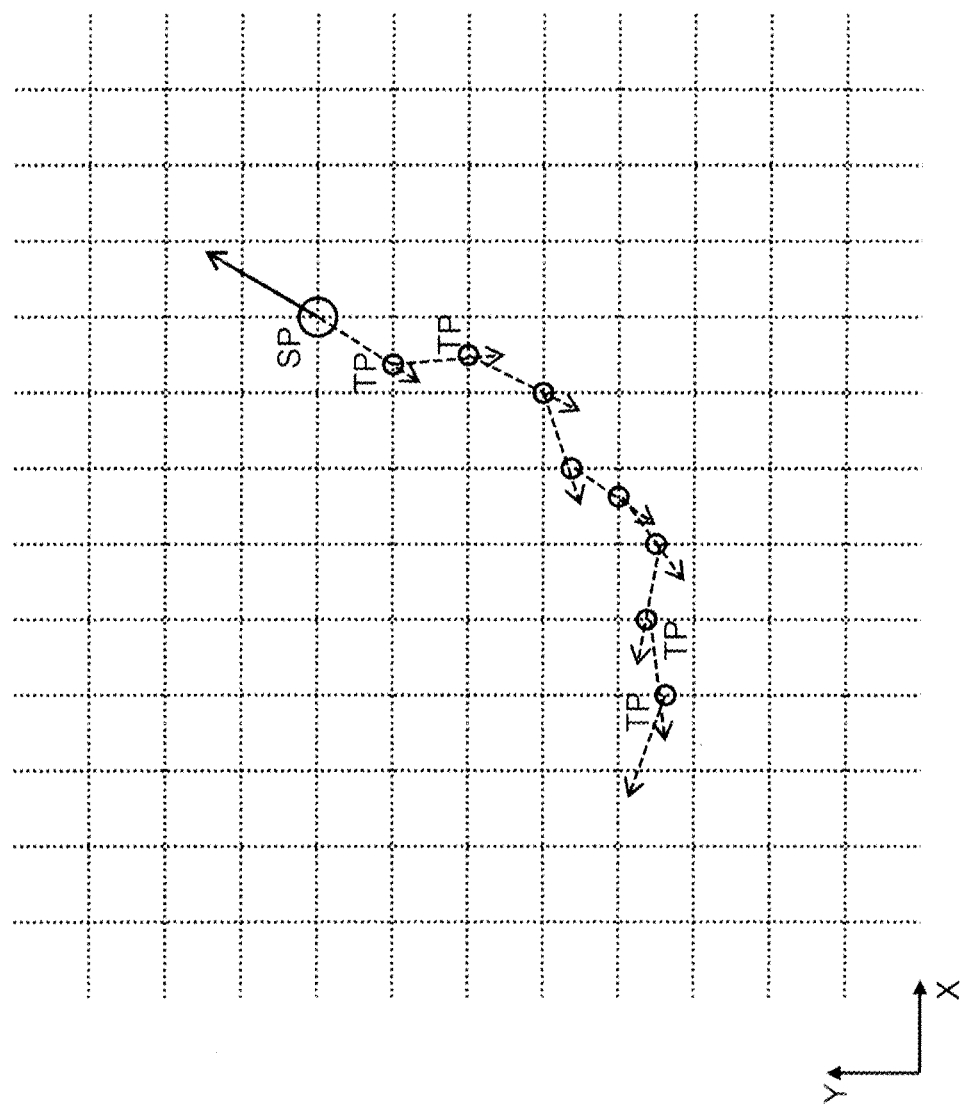
FIG. 3 is a diagram for explaining specific example processing for inversely tracking a flow of fluid.

FIG. 3 is a diagram for explaining specific example processing for inversely tracking the flow of fluid. The streamline forming unit 50 places a plurality of initial start points SP discretely within a region of interest to be diagnosed, over a whole region within a cardiac cavity, for example, and, from each of the initial start points SP, inversely tracks the flow of fluid in accordance with the two-dimensional velocity vector distribution. FIG. 3 illustrates only one representative example initial start point SP.

The streamline forming unit 50 starts tracking from the initial start point SP in the direction opposite (an arrows in dashed line) the velocity vector at the initial start point SP (an arrow in solid line) to search for a tracking point TP. The tracking point TP is searched for on an operation grid in a lattice shape, for example. After locating the tracking point TP on the operation grid, tracking is continued in the direction opposite the velocity vector at the tracking point TP (an arrow in dashed line), to search for the next tracking point TP.

When a velocity vector does not exist at the location of the tracking point TP, an interpolated vector is obtained by interpolation processing or other processing, based on a plurality of velocity vectors near the tracking point TP which have already been computed, and is designated as the velocity vector at the tracking point TP. Then, the tracking is continued in the direction opposite the velocity vector.

Thus, as illustrated in FIG. 3, the tracking points TP located in the direction opposite the velocity vector are sequentially searched for from one initial start point SP, to inversely track the flow of fluid by sequentially tracking the plurality of tracking points TP. The streamline forming unit 50 then designates as a proper start point the tracking point TP located when a termination condition of the inverse tracking is satisfied.

The streamline forming unit 50 executes the inverse tracking processing within a region of interest set with respect to the cardiac cavity of the heart, for example, and designates the tracking point TP found when the result of the inverse tracking reaches a boundary of the region of interest, as a proper start point. The streamline forming unit 50 may designate, as a proper start point, the tracking point TP found when the velocity vector is equal to or less than the lower limit reference value in the course of the inverse tracking or the tracking point TP found when the length (distance) of the inverse tracking reaches the upper limit value in the course of tracking. The proper start point may also be determined according to a composite termination condition including a combination of a plurality of termination conditions.

The streamline forming unit 50 disposes a plurality of initial start points SP at intersections of an operation grid in a lattice shape, for example, within a region of interest to be diagnosed, over a whole region within a cardiac cavity of the heart, and, for each of the initial start points SP, searches for the proper start point by inverse tracking.

Figure 4:
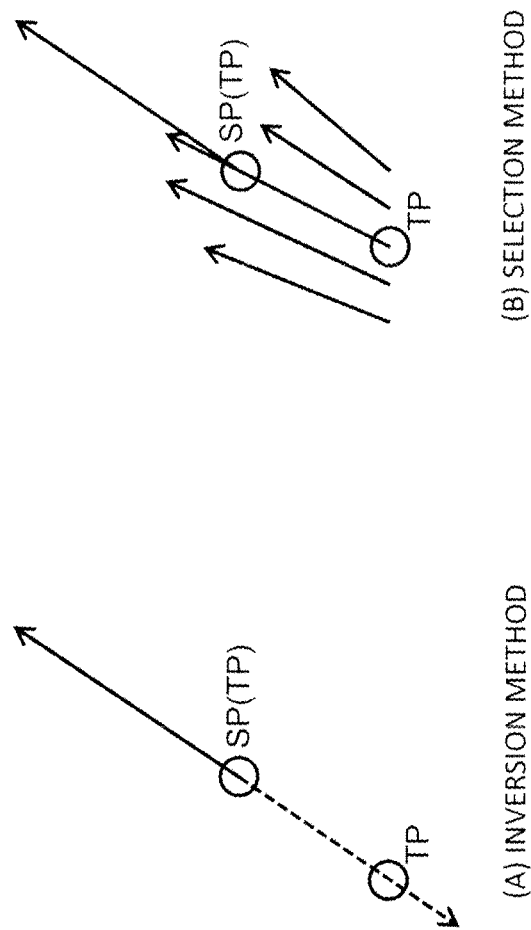
FIG. 4 explains specific examples for determining a tracking point by inverse tracking.

FIG. 4 explains specific examples for determining the tracking point by inverse tracking. The streamline forming unit 50 may use an inversion method (A) and a selection method (B) for inversely tracking the flow of fluid while sequentially tracing the tracking points TP located in the direction opposite the motion vectors (velocity vectors) from the initial start point SP.

According to the inversion method (A), with reference to the velocity vector (an arrow in solid line) at the initial start point SP (or the tracking point TP already obtained), tracking proceeds from the initial start point SP (or the tracking point TP) in the direction of an inversion vector (an arrow in dashed line) of the velocity vector, to search for a tracking point TP on the operation grid in a lattice shape, for example. The streamline forming unit 50 may use the selection method (B) in place of the inversion method (A) or in combination with the inversion method (A).

According to the selection method (B), among a plurality of velocity vectors (arrows in solid lines) on the operation grid near the initial start point SP (or the tracking point TP already obtained), a single velocity vector directed to the initial start point SP (or the tracking point obtained last) is selected, and the origin (a point on the operation grid) of the velocity vector is designated as a tracking point TP.

The streamline forming unit 50, upon locating the proper start point by inversion tracking, then forms a streamline extending from the proper start point.

Figure 5:
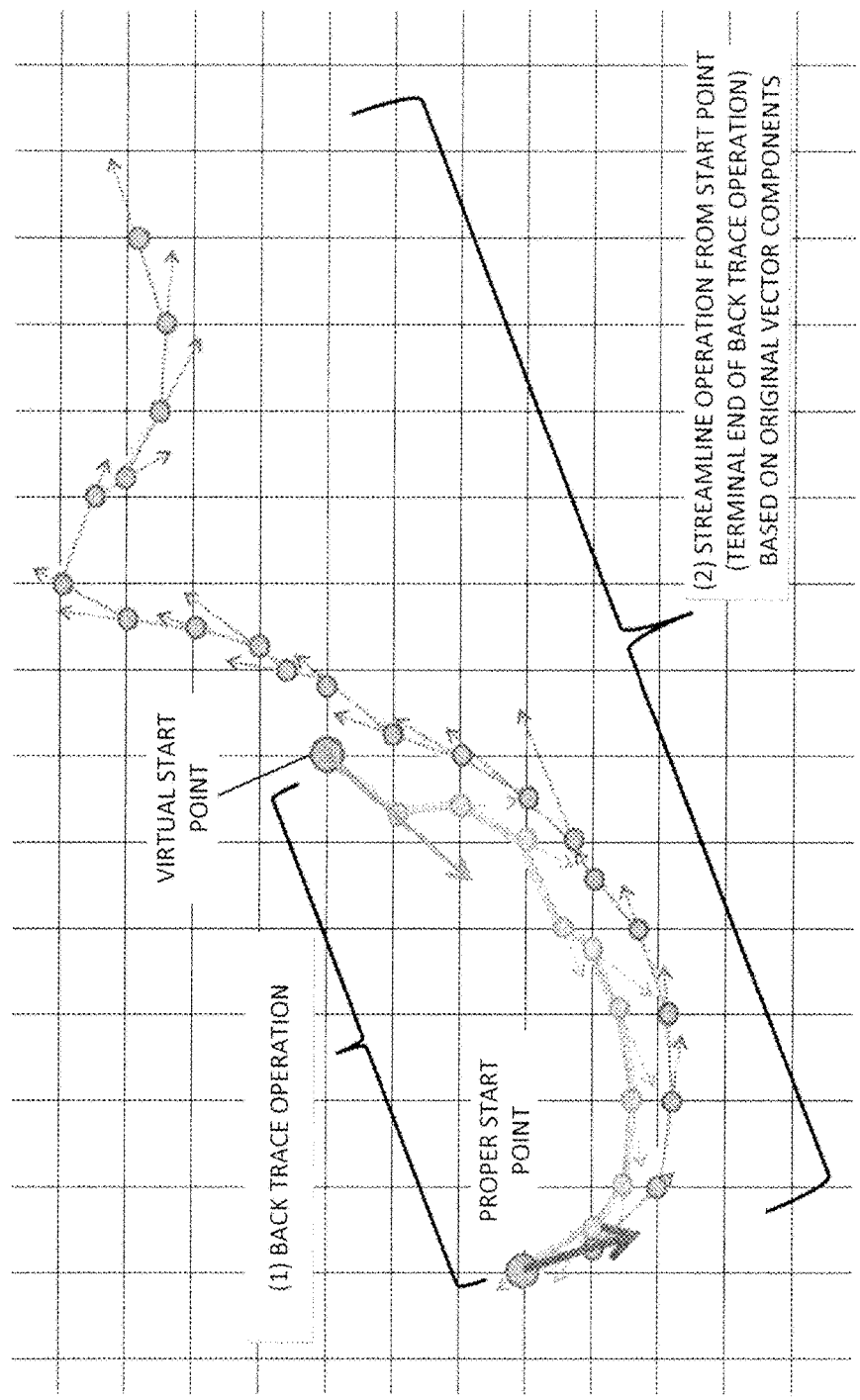
FIG. 5 is diagram illustrating a specific example streamline extending from a proper start point.

FIG. 5 is a diagram illustrating a specific example streamline extending from the proper start point. The streamline forming unit 50 designates the initial start point as a virtual start point, and the performs the back trace operation, that is, the inverse tracking processing described above with reference to FIG. 3, from the virtual start point, to search for the proper start point.

After locating the proper start point, the streamline forming unit 50 performs the forward trace operation using original vector components, that is, the tracking processing described above with reference to FIG. 2, thereby sequentially tracking a plurality of tracking points from the proper start point. The streamline forming unit 50 further connects adjacent points of the proper start point and the plurality of tracking points with a straight line or a curved line, to thereby form a polygonal or curved streamline.

The streamline forming 50 may track, from the initial start point (virtual start point), a plurality of tracking points based on the forward trace operation using the original vector components and connect adjacent points of the initial start point and the plurality of tracking points with a straight line or a curved line to thereby form a streamline downstream from the initial start point. The streamline forming 50 may further inversely track, from the initial start point, a plurality of tracking points by the inverse tracking to locate the proper start point and connect adjacent points among the plurality of tracking points and the proper start point with a straight line or a curved line to thereby form a streamline upstream of the initial start point to the proper start point. The streamline forming 50 may then connect the upstream streamline and the downstream streamline together, thereby forming a streamline extending from the proper start point through the initial start point toward the downstream direction.

Once the streamlines are formed by the streamline forming unit 50, the display processing unit 60 forms a display image of the streamlines.

FIG. 6 illustrates specific example display images of the streamlines. The display processing unit 60, based on the image data of the ultrasound image formed by the image forming processing unit 20 and the streamlines formed by the streamline forming unit 50, forms a display image indicating a plurality of streamlines within a B-mode image representing a heart cavity, for example.

In FIG. 6, a comparative example is a specific example display image indicating a plurality of streamlines extending from a plurality of initial start points. More specifically, in the comparative example, the proper start point is not located, and the streamlines are not formed upstream from the initial start points. Consequently, the streamlines extend from the initial start points set within a region of interest, that is, inside the heart cavity, and are therefore interrupted at these initial start points, so that the streamlines appear to be flowing out from these initial start points. Further, the number of streamlines increases toward downstream, and the density of the streamlines also increases toward downstream.

On the other hand, a display example in FIG. 6 is a specific example display image indicating a plurality of streamlines extending from a plurality of proper start points. In the display example in FIG. 6, a plurality of proper start points have been searched for under a condition that the search is terminated upon reaching the boundaries of the region of interest set with respect to the heart cavity, for example, and a plurality of streamlines extending from the plurality of proper start points are formed. This structure substantially (or completely, if possible) eliminates a possibility of interruption of the streamlines within the region of interest, that is, inside the heart cavity, and also substantially (or completely, if possible) eliminates a possibility of increasing the density of the streamlines toward downstream. Thus, continuous and natural streamlines can be formed.

The display processing unit 60 may also apply, to the streamlines formed by the streamline forming unit 50, display processing in accordance with the direction of flow on the streamlines to form a display image of the streamlines Preferable display processing includes figures (e.g., triangle) and symbols (e.g., arrow) indicating the direction of flow.

Figure 7:
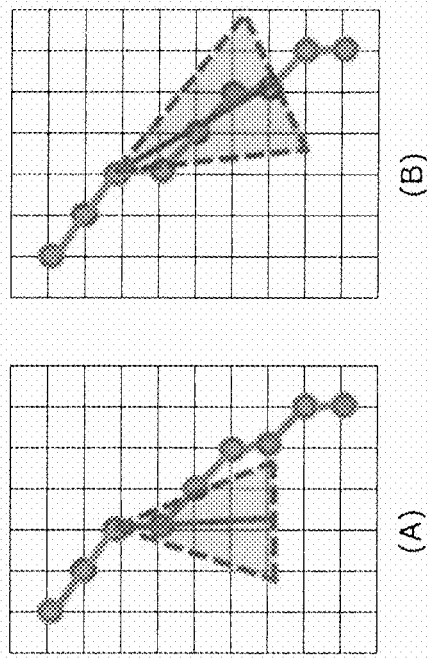
FIG. 7 illustrates specific example display processing in accordance with a direction of a flow.

FIG. 7 illustrates specific example display processing in accordance with the direction of the flow. In a specific example (A), a triangle is formed from two adjacent tracking points on the streamline. For example, along a straight line passing through the two adjacent tracking points, an isosceles triangle extending from the upstream tracking point toward the downstream tracking point is formed. An arrow directed toward the downstream tracking point from the upstream tracking point, for example, may alternatively be formed. Use of these figures enables display of the local flow direction between the two adjacent tracking points.

A specific example (B), on the other hand, is an isosceles triangle formed by tracking back some tracking points on the streamline toward upstream from the tracking point corresponding to the vertex of the isosceles triangle, and designating the location of a tracking point several points away from the start point as a base of the triangle. Thus, an average flow direction between the two tracking points away from each other can be indicated. Alternatively, an arrow may be formed from the tracking point corresponding to the base toward the tracking point corresponding to the vertex, for example.

The display processing unit 60, based on the specific example (A) or (B), for example, forms a display in accordance with the directions of the flows at a plurality of locations on each streamline. The display processing unit 60 may be configured to allow the user such as a doctor to select the specific example (A) or (B).

Figure 8:
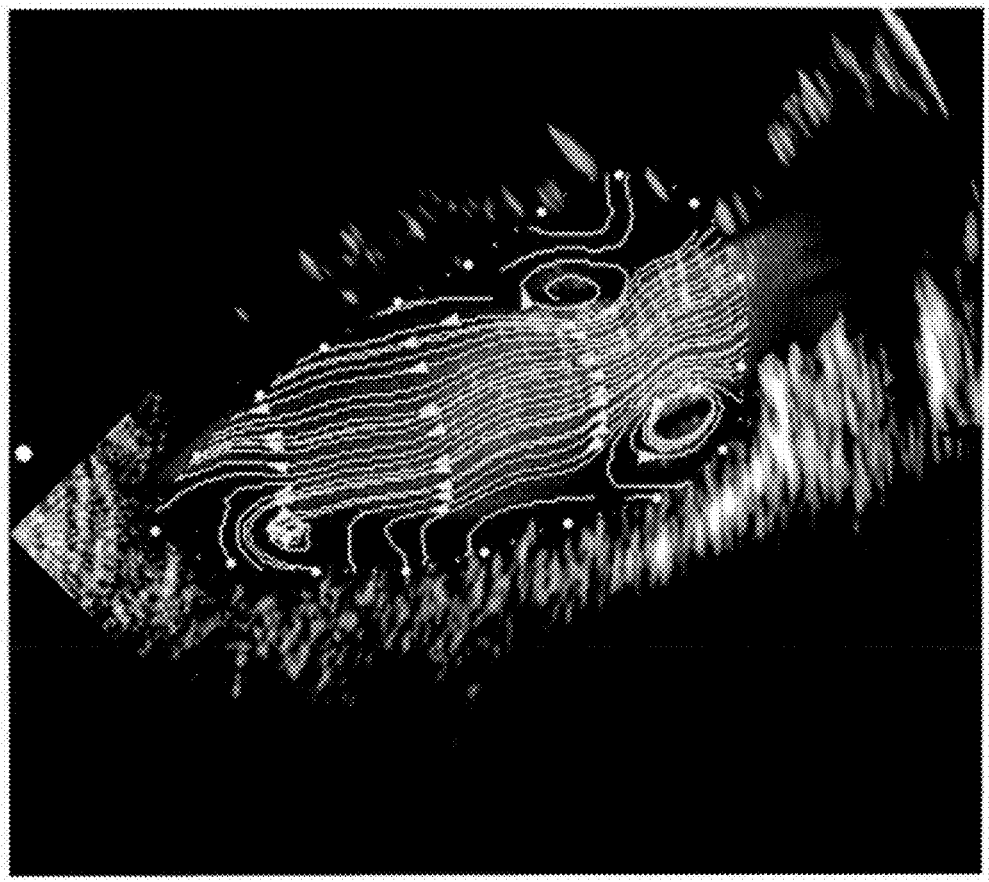
FIG. 8 is a diagram illustrating a specific example display image indicating directions of flows on streamlines.

FIG. 8 is a diagram illustrating a specific example display image indicating the directions of the flows on the streamlines. The display processing unit 60 forms triangles (or arrows) in accordance with the flow directions at a plurality of locations on each of the streamlines. The triangles (or arrows) may be formed at fixed intervals or at locations where the flow direction significantly changes, for example, on each streamline. The triangles or other symbols may be formed at locations designated by the user such as a doctor.

The display processing unit 60 may further apply, to each streamline, display processing in accordance with the flow velocity on the streamline, and form a display image of the streamline. The display processing unit 60 may, for example, apply coloring processing in accordance with the magnitude of the velocity vector at each of a plurality of locations on each streamline and form a display image of the streamline with different colors in accordance with the flow velocity.

The display processing unit 60 may further represent each velocity vector by an arrow or other symbol, in addition to or in place of the streamline, to thereby display a distribution image of the velocity vectors.

The ultrasonic diagnostic device according to a preferable embodiment of the present invention has been described above. At least one of the velocity vector computation unit 40, the streamline forming unit 50, and the display processing unit 60, for example, illustrated in FIG. 1, may be implemented by a computer, which may be then caused to function as a fluid information processing device.

It should be noted that the embodiments described above are only examples in all respects and shall not limit the scope of the present invention. The present invention may include various modifications within a scope which does not depart from its spirit.

REFERENCE SIGNS LIST 10 probe, 12 transmitter and receiver unit, 20 image forming processing unit, 30 Doppler processing unit, 40 velocity vector computation unit, 50 streamline forming unit, 60 display processing unit, 70 control unit.

The invention claimed is:
1. An ultrasonic diagnostic device, comprising:
a probe configured to transmit and receive an ultrasonic wave;
a transmitter and receiver unit configured to control the probe to obtain the received signal of the ultrasonic wave from an interior of a living body;
a Doppler processing unit configured to measure Doppler information of the interior of the living body based on the received signal of the ultrasonic wave;
a vector computation unit configured to calculate a distribution of motion vectors of fluid in the living body based on the Doppler information of the interior of the living body; and
a streamline forming unit configured to form a streamline indicating a flow of the fluid based on the distribution of the motion vectors by inversely tracking the flow of the fluid from an initial start point in a direction opposite the motion vectors to search for an upstream start point and forming a streamline extending from the upstream start point;
wherein the Doppler processing unit, the vector computation unit, and the streamline forming unit are constructed, at least in part, as hardware.
2. The ultrasonic diagnostic device according to claim 1, wherein
the streamline forming unit is configured to inversely track the flow of the fluid by sequentially tracing back a tracking point located in the direction opposite the motion vectors from the initial start point.
3. The ultrasonic diagnostic device according to claim 2, wherein
the streamline forming unit is configured to designate the tracking point which satisfies a condition for terminating inverse tracking as the upstream start point.
4. The ultrasonic diagnostic device according to claim 3, wherein the streamline forming unit is configured to track the flow of the fluid in a direction of the motion vectors from the upstream start point to thereby form a streamline extending from the upstream start point.

5. The ultrasonic diagnostic device according to claim 3, wherein
the streamline forming unit is configured to inversely track the flow of the fluid in the direction opposite the motion vectors from the initial start point to form an upstream streamline from the initial start point to the upstream start point, to track the flow of the fluid in a direction of the motion vectors from the initial start point to form a downstream streamline from the initial start point, and to connect the upstream streamline and the downstream streamline to form a streamline extending from the upstream start point toward downstream through the initial start point.

6. The ultrasonic diagnostic device according to claim 2, wherein
the streamline forming unit is configured to track the flow of the fluid in a direction of the motion vectors from the upstream start point to thereby form a streamline extending from the upstream start point.

7. The ultrasonic diagnostic device according to claim 2, wherein
the streamline forming unit is configured to inversely track the flow of the fluid in the direction opposite the motion vectors from the initial start point to form an upstream streamline from the initial start point to the upstream start point, to track the flow of the fluid in a direction of the motion vectors from the initial start point to form a downstream streamline from the initial start point, and to connect the upstream streamline and the downstream streamline to form a streamline extending from the upstream start point toward downstream through the initial start point.

8. The ultrasonic diagnostic device according to claim 1, wherein
the streamline forming unit is configured to track the flow of the fluid in a direction of the motion vectors from the upstream start point to thereby form a streamline extending from the upstream start point.

9. The ultrasonic diagnostic device according to claim 8, wherein display processing is applied, to the streamline formed by the streamline forming unit, in accordance with the direction of the flow on the streamline to form a display image of the streamline.

10. The ultrasonic diagnostic device according to claim 1, wherein
the streamline forming unit is configured to inversely track the flow of the fluid in the direction opposite the motion vectors from the initial start point to form an upstream streamline from the initial start point to the upstream start point, to track the flow of the fluid in a direction of the motion vectors from the initial start point to form a downstream streamline from the initial start point, and to connect the upstream streamline and the downstream streamline to form a streamline extending from the upstream start point toward downstream through the initial start point.

11. The ultrasonic diagnostic device according to claim 10, wherein display processing is applied, to the streamline formed by the streamline forming unit, in accordance with the direction of the flow on the streamline to form a display image of the streamline.

12. The ultrasonic diagnostic device according to claim 10, wherein display processing is applied, to the streamline formed by the streamline forming unit, in accordance with a flow rate on the streamline to form a display image of the streamline.

13. The ultrasonic diagnostic device according to claim 1, wherein display processing is applied, to the streamline formed by the streamline forming unit, in accordance with the direction of the flow on the streamline to form a display image of the streamline.

14. The ultrasonic diagnostic device according to claim 1, wherein display processing is applied, to the streamline formed by the streamline forming unit, in accordance with a flow rate on the streamline to form a display image of the streamline.

15. A fluid information processing device, comprising:
a vector computation unit configured to calculate, based on Doppler information received from a living body using ultrasonic waves, a distribution of motion vectors of fluid within the living body; and
a streamline forming unit configured to form a streamline indicating a flow of the fluid based on the distribution of motion vectors by inversely tracking the flow of the fluid from an initial start point in a direction opposite the motion vectors to search for an upstream start point and forming a streamline extending from the upstream start point;
wherein the vector computation unit and the streamline forming unit are constructed at least in part, as hardware.

* * * * *